United States Patent [19]

Suskovic et al.

[11] Patent Number: 5,064,812
[45] Date of Patent: Nov. 12, 1991

[54] METAL COMPLEXES OF N-ACETYL-GLUCOSAMINYL-N-ACETYL-MURAMOYL-L-ALANYL-D-ISOGLUTAMI-NYL-(L)-MESO-DIAMINO-PIMELYL-(D-AMIDE)-(L)-D-ALANYL-D-ALANINE AND THEIR USE IN PHARMACEUTICALS

[75] Inventors: Bozidar Suskovic; Zlatko Vajtner; Radmila Naumski, all of Zagreb, Yugoslavia

[73] Assignee: Sour Pliva, Yugoslavia

[21] Appl. No.: 443,839

[22] Filed: Dec. 4, 1989

Related U.S. Application Data

[63] Continuation of Ser. No. 122,824, Nov. 19, 1987.

[30] Foreign Application Priority Data

Nov. 16, 1986 [YU] Yugoslavia ............................ 1982/86

[51] Int. Cl.$^5$ ............................................. A61K 37/02
[52] U.S. Cl. ......................................... 514/8; 514/322
[58] Field of Search ............................. 514/8; 530/322

[56] References Cited

U.S. PATENT DOCUMENTS 4,545,932 10/1985 Takase et al. ...................... 530/322

OTHER PUBLICATIONS

Hoyle et al., Metal Binding by the Peptidoglycan Sacculus of *E. coli* K—12, *Can J. Microbiol*, vol. 30, 1984, 204.

Klaic, B. $^{13}$C—N.m.r. Studies of a natural immunoadjuvant, pephdoglycan monomer and related compounds.

Sigel et al. Coordinating Prop of the Amide Bond. Stability & Strut of metal Ion Complexes of Peptides & Rel. Ligands, *Chem Rev.* 1982.

*Primary Examiner*—John Doll
*Assistant Examiner*—Choon Koh
*Attorney, Agent, or Firm*—Pollock, Vande Sande & Priddy

[57] ABSTRACT

A complex of N-acetyl-glucosaminyl-N-acetyl-muramoyl-L-alanyl-D-isoglotaminyl- (L)-meso-diamino-pimelyl-(D-amide)-D-alanyl-D-alanine with bivalent metals chosen from the group comprising $Cu^{2+}$, $Zn^{2+}$, $Co_{hu 2+}$; $Ni^{2+}$ and $Cd^{2+}$ in the molar ratio of the organic ligand: $Cu^{2+}=2:1$ and the organic ligand: $Zn^{2+}$ or $Co^{2+}$ or $Ni^{2+}$ or $Cd^{2+}=1:1$, compositions containing it and their use in the treatment of immunological insufficiencies and disturbances in humans and animals.

9 Claims, No Drawings

METAL COMPLEXES OF N-ACETYL-GLUCOSAMINYL-N-ACETYL-MURAMOYL-L-ALANYL-D-ISOGLUTAMINYL-(L)-MESO-DIAMINO-PIMELYL-(D-AMIDE)-(L)-D-ALANYL-D-ALANINE AND THEIR USE IN PHARMACEUTICALS

This application is a continuation of Ser. No. 07/122,824 filed on Nov. 19, 1987.

The present invention relates to new, biologically active immunoadjuvants, more specifically to new metal complexes of N-acetyl-glucosaminyl-N-acetyl-muramoyl-L-alanyl-D-isoglutaminyl-(L)-meso-diamino-pimelyl-(D-amide)-(L)-D-alanyl-D-alanine with bivalent metals and to their use in pharmaceuticals.

It has been known (YU patent 35 040) that the submerse cultivation of the bacteria *Brevibacterium divaricatum* NRRL-2311 and *Micrococcus glutamicus* ATCC-13287 in the presence of inhibitors of cell wall biosynthesis yields peptidoglycan fragments, from which there is, subsequently to the incubation with a lysozyme and the fractionation on molecular sieves, isolated the well-defined peptidoglycan monomer N-acetyl-glucosaminyl-N-acetyl-muramoyl-L-alanyl-D-isoglutaminyl-(L)-meso-diamino-pimelyl-(D-amide)-(L)-D-alanyl-D-alanine (abbreviated PMG) (YU patent application P 761/77; AT patent 362 740; Carbohydr. Res. 110 (1982), 320–325), exhibiting a significant immunostimulating (Z. Immun.-Forsch. 155 (1979); 312–318; Periodicum Biologorum 82 (1980), 147–151) and antimetastatic activity (Eur. J. Cancer Oncol. 19 (1983), 681–686; Cancer Immunol. Immunother. 15 (1983), 84–86; Cancer Immunol. Immunother. 18 (1984), 49–53) with practically no toxicity or pyrogenicity.

It has also been known that the presence of metals and the formation of metal complexes might substantially influence the stability, distribution, biotransformation, elimination and other characteristics of pharmaceutically active substances.

In literature there has been extensively described the formation, the stability and the structure of metal complexes of peptides (e.g. *Chem. Rev.* 82 (1982) 385–426), whereas for the peptidoglycan sacculus from the *E. coli* K-12 it has been said that it eliminates from an aqueous solution $\geq 1$ μm of the metal for each mg of the dry product (*Can. J. Microbiol.* 30 (1984), 204–211).

The metal complexes of N-acetyl-glucosaminyl-N-acetyl-muramoyl-L-alanyl-D-isoglutaminyl-(L)-meso-diamino-pimelyl-(D-amide)-(L)-D-alanyl-D-alanine have, according to the Applicant's own knowledge and search of the prior art, not been described as yet.

There have now been found new useful complexes of N-acetyl-glucosaminyl-N-acetyl-muramoyl-L-alanyl-D-isoglutaminyl-(L)-meso-diamino-pimelyl-(D-amide)-(L)-D-alanyl-D-alanine of the formula

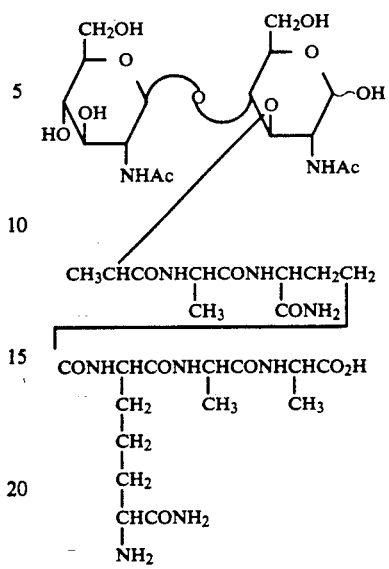

I with bivalent metals chosen from the group comprising $Cu^{2+}$, $Ni^{2+}$, $CO^{2+}$, $Cd^{2+}$ and $Zn^{2+}$ in the molar ratio of ligand:metal ($Ni^{2+}$, $Co^{2+}$, $Cd^{2+}$ and $Zn^{2+}$)=1:1 or ligand:$Cu^{2+}$=2:1, which exhibit a superior pharmacological, specifically a potent immunological activity.

The new inventive metal complexes of the compound of formula I may be prepared by means of the reaction of the compound (I) with suitable water-soluble salts of the afore-cited bivalent metals in an aqueous solution and at ambient temperature. The pH of the reaction solution is adjusted within the limiting values of 6 to 9 by the addition of aqueous solutions of alkali hydroxides, whereupon the aqueous solution is concentrated and the product is precipitated therefrom by the addition of a water-soluble solvent and finally by filtration.

The molar ratio of the ligand:metal is 2:1 in the preparation of the $Cu^{2+}$-complex and 1:1 for $Zn^{2+}$, $Co^{2+}$, $Ni^{2+}$ or $Cd^{2+}$.

The activity of the present inventive complexes as immunoadjuvants was assessed on CBA/H mice by means of the PFC (plaque-forming-cells) technique (Jerne et al, in: Cell Bound Antibodies, Whister Institute Press, Philadelphia 1963, p. 109).

As evident from the data presented in the following Examples, they exhibit a useful pharmacological, e.g. an immunostimulating, immunomodulating and immunoadjuvant activity.

Pharmaceutical compositions, both veterinary and human, containing the subject metal complexes appropriate in the treatment of immunological insufficiency and disturbances, are prepared by methods and may contain excipients which are well known in the art.

The exact regimen for administering the compounds and compositions disclosed herein will necessarily depend upon the needs of the individual subject being treated and the type of treatment.

The administration of injection formulations of the claimed complexes has been tested and has given favorable results.

The present invention is illustrated by the following Examples, which, however, do not limit its scope in any way.

EXAMPLE 1

N-acetyl-glucosaminyl-N-acetyl-muramoyl-L-alanyl-D-isoglutaminyl-(L)-meso-diamino-pimelyl-(D-amide)-(L)-D-alanyl-D-alanine (PGM) (I) (201.8 mg; 0.2 mmole) was dissolved in water (10 ml) and there was added $CuCl_2 \times 2\ H_2O$ (17 mg; 0.1 mmole). It was kept stirring for 1 hour, whereupon the pH was adjusted to 6.8 by the addition of 0.1N NaOH and stirred on for an additional hour. The reaction solution was concentrated by means of evaporation under reduced pressure to a volume of about 4 ml and the product was precipitated therefrom under stirring and dropwise addition of acetone. The precipitate was aspirated, washed with acetone and dried in high vacuum for 4 hours.

There were obtained 200 mg of the Cu complex (90%).

Cu analysis (atom absorption spectrophotometric method): Calc.: 3.05%. Found: 3.02%.

The complex exhibited a statistically significant immunostimulation (143%).

EXAMPLE 2

The process was performed as described in Example 1 with the sole exception that $NiCl_2 \times 6\ H_2O$ (48 mg, 0.2 mmole) was charged instead of Cu chloride and that sodium lye was added until there was adjusted a pH of 7.5. There were obtained 222 mg (89%) of a light green product.

Ni analysis (polarographic method, 0.1N KCl, $E_{\frac{1}{2}} = -1.1$ V; SCE—saturated calomel electrode): Calc.: 5.50. Found: 5.42.

The produced complex exhibited a statistically significant immunomodulation (205%).

EXAMPLE 3

The process was performed as described in Example 1 with the sole exception that $CoCl_2 \times 6\ H_2O$ (48 mg, 0.2 mmole) was charged instead of Cu chloride and that sodium lye was added until there was adjusted a pH of 8.2. There were obtained 200 mg of a light blue product (80%).

Co analysis (polarographic method, 0.1N KCl, $E_{\frac{1}{2}} = -1.25$ V; SCE): Calc.: 5.52%. Found: 5.48%.

The complex exhibited an immunoadjuvant activity (143%).

EXAMPLE 4

The process was performed as described in Example 1 with the sole exception that $CdSO_4 \times 8/3\ H_2O$ (51.3 mg, 0.2 mmole) was charged instead of Cu chloride and that sodium lye was added until there was adjusted a pH of 8.2. There were obtained 175 mg (75%) of a white product.

Cd analysis (polarographic method, 0.1N HCl–0.1N KCl (1:25), $E_{\frac{1}{2}} = -0.70$ V; SCE):

The complex exhibited an immunoadjuvant activity (98%).

EXAMPLE 5

The process was performed as described in Example 1 with the sole exception that $ZnCl_2$ (27.3 mg, 0.2 mmole) was charged instead of Cu chloride and that sodium lye was added until there was adjusted a pH of 7.5. There were obtained 160 mg (70%) of a white product.

Zn analysis (polarographic method, 0.1N HCl–0.1 KCl (1:25); $E_{\frac{1}{2}} = -1.25$ V, SCE); Calc.: 6.08%. Found: 6.0%.

The complex exhibited an immunoadjuvant activity (121%).

What is claimed is:

1. A complex of N-acetyl-glucosaminyl-N-acetyl-muramoyl-L-alanyl-D-isoglutaminyl-(L)-meso-diamino-pimelyl-(D-amide)-(L)-D-alanyl-D-alanine of the formula

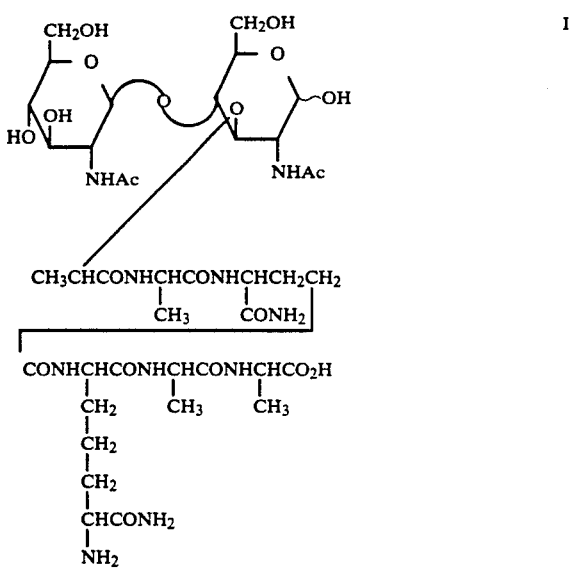

with bivalent metals chosen from the group comprising $Cu^{2+}$, $Zn^{2+}$, $Co^{2+}$, $Ni^{2+}$ and $Cd^{2+}$ in the molar ratio of the organic ligand:$Cu^{2+}=2:1$ and the organic ligand:$Zn^{2+}$ or $Co^{2+}$ or $Ni^{2+}$ or $Cd^{2+}=1:1$.

2. The complex of claim 1 wherein said bivalent metal includes $Zn^{2+}$.

3. The complex of claim 1 wherein said bivalent metal includes $Co^{2+}$.

4. The complex of claim 1 wherein said bivalent metal includes $Ni^{2+}$.

5. The complex of claim 1 wherein said bivalent metal includes $Cd^{2+}$.

6. The complex of claim 1 wherein said bivalent metal includes $Cu^{2+}$.

7. The complex of claim 1 being a complex of N-acetyl-glucosaminyl-N-acetyl-muramoyl-L-alanyl-D-isoglutaminyl-(L)-meso-diamino-pimelyl-(D-amide)-(L)-D-alanyl-D-alanine.

8. A pharmaceutical composition, which comprises an effective amount of a complex as claimed in claim 1.

9. A method of treating immunological insufficiency and/or disturbances in humans and animals, which comprises administering an effective amount of a complex as claimed in claim 1 or a composition containing same as an active ingredient.

* * * * *